United States Patent [19]

Zhang et al.

[11] Patent Number: 5,543,099
[45] Date of Patent: Aug. 6, 1996

[54] PROCESS TO MANUFACTURE MICRONIZED NIFEDIPINE GRANULES FOR SUSTAINED RELEASE MEDICAMENTS

[75] Inventors: Guohua Zhang, Parsippany; Prasad Pinnamaraju, Edison, both of N.J.

[73] Assignee: Hallmark Pharmaceutical, Inc., Somerset, N.J.

[21] Appl. No.: 314,727

[22] Filed: Sep. 29, 1994

[51] Int. Cl.⁶ ........................................ B29B 9/16
[52] U.S. Cl. ........................ 264/115; 264/117; 264/122; 424/470
[58] Field of Search .................... 264/115, 122, 264/117; 424/470

[56] References Cited

U.S. PATENT DOCUMENTS

| | | |
|---|---|---|
| Re. 33,963 | 6/1992 | Hegasy . |
| 4,122,157 | 10/1978 | Huber ........................................ 424/472 |
| 4,666,705 | 5/1987 | De Crosta et al. . |
| 4,786,503 | 11/1988 | Edgren et al. . |
| 4,814,175 | 3/1989 | Tack et al. . |
| 4,871,548 | 10/1989 | Edgren et al. . |
| 4,880,623 | 11/1989 | Piergiorgio et al. ................... 424/470 |
| 4,882,144 | 11/1989 | Hegasy . |
| 4,952,402 | 8/1990 | Sparks et al. . |
| 5,057,317 | 10/1991 | Iida ........................................ 424/470 |
| 5,108,757 | 4/1992 | Erdos et al. . |
| 5,264,446 | 11/1993 | Hegasy . |
| 5,266,581 | 11/1993 | Schmidt et al. . |

FOREIGN PATENT DOCUMENTS

| | | |
|---|---|---|
| 0047899 | 3/1982 | European Pat. Off. . |
| 0078430 | 5/1983 | European Pat. Off. . |
| 2822882 | 12/1978 | Germany . |
| 3142853 | 5/1983 | Germany . |
| 58-109412 | 6/1983 | Japan . |
| 2139892A | 11/1984 | United Kingdom . |

*Primary Examiner*—Robert A. Dawson
*Assistant Examiner*—Kenneth M. Jones
*Attorney, Agent, or Firm*—Richard C. Litman

[57] ABSTRACT

The subject invention is a process to manufacture a sustained release pharmaceutical tablet. The process includes granulation of inactive ingredients, such as hydroxypropyl cellulose, with active ingredients, such as nifedipine; followed by micronization of the granules. Additional granulation of further active or inactive ingredients is done with or without the micronized granules formed in the first step. All of the granules are then dried if necessary, lubricated, and compressed into tablets which slowly release the active ingredient over a controlled length of time.

21 Claims, No Drawings

5,543,099

PROCESS TO MANUFACTURE MICRONIZED NIFEDIPINE GRANULES FOR SUSTAINED RELEASE MEDICAMENTS

BACKGROUND OF THE INVENTION

1. Field of the Invention

The present invention relates to a process to manufacture sustained release tablets of a therapeutically active ingredient. More specifically, the present invention is a novel approach to prepare a micronized granulation containing both active and inactive ingredients which can be formulated into a sustained release tablet.

2. Description of the Prior Art

Both for the patient and the physician, sustained release dosage forms, in general, are a great advantage over immediate release dosage forms because they allow a therapeutically effective amount of an active ingredient to be continuously delivered over an extended period of time with a minimum number of daily doses, in some instances as few as one dose per day. A common approach to impart sustained release characteristics to a solid pharmaceutical formulation is to coat the active ingredient with a relatively insoluble coating, or to embed the active ingredient in a resinous matrix. The slow diffusion of drug, or erosion of the coating or the matrix then releases the active ingredient. Various approaches have been described in the patent literature, a representative sampling of which appears below.

U.S. Pat. No. 4,666,705, issued May 19, 1987, to De Crosta et al, describes a controlled release pharmaceutical formulation in the form of a tablet which includes an active agent and an acrylic acid polymer or copolymer. The tablet is formed via a dry granulation technique and does not require a coating.

U.S. Pat. No. 4,786,503, issued Nov. 22, 1988, to Edgren et al, describes a pharmaceutical dosage form having two lamina disposed adjacent one another to form a tablet. The lamina may contain both active and inactive ingredients such that the release characteristics of the resultant tablet may be controlled by the arrangement of the lamina. Each of the lamina are composed of at least one type of hydroxypropylmethyl cellulose. Celluloses having differing degrees of polymerization (DP) are also used to control release of the active agent. A related composition is described by Edgren et al in U.S. Pat. No. 4,871,548, issued Oct. 3, 1989.

U.S. Pat. No. 4,814,175 issued Mar. 21, 1989, to Tack et al, describes a combination pharmaceutical containing nifedipine and mepindolol. The nifedipine and mepindolol are granulated separately using conventional excipients via a wet or dry granulation process. The separate granules are then placed within hard gelatin capsules for oral consumption.

U.S. Pat. No. 4,882,144, issued Nov. 21, 1989; and the resulting Reissued Patent, U.S. Pat. No. 33,963, issued Jun. 16, 1992 to Hegasy; as well as U.S. Pat. No. 5,264,446, issued 23, 1993, to Hegasy et al, describe a solid pharmaceutical composition containing dihydropyridines, and processes for their production. Specifically, Hegasy describes the dissolution of nifedipine and polyvinylpyrrolidone (PVP) in a limited amount of organic solvent to form a viscous slush containing nifedipine and PVP. The slush is then mixed with a cross-linked, insoluble polyvinylpyrrolidone (PVPP) to cause agglomeration. This agglomerated mixture is then compressed into tablets in which the nifedipine (or other dihydropyridine active agent) is uniformly spread throughout the tablet.

Another pharmaceutical composition containing dihydropyridines, PVP and insoluble PVPP is described by Schmidt et al in U.S. Pat. No. 5,266,581, issued Nov. 30, 1993. Here, the dihydropyridine and the PVP are dissolved in a suitable organic solvent, and a wetting agent is added thereto. Insoluble PVPP is then added to the mixture, and the mixture is granulated. The granules so formed are then further processed into tablets with the inclusion of various conventional additives.

U.S. Pat. No. 4,952,402, issued Aug. 28, 1990, to Sparks et al, describes a controlled release powder for edible and pharmaceutical formulations. The composition includes micro-particles of a pre-determined size (0.1 to 125 micrometers) which define a matrix of an inert polymer with an active agent uniformly dispersed therein. The dissolution rate of the inert polymer matrix causes the sustained release of the active agent.

U.S. Pat. No. 5,108,757, issued Apr. 28, 1992, to Erdos et al describes a process similar to Schmidt et al, above, except that instead of directly granulating the PVP/nifedipine mixture with insoluble PVPP, wetting agents and retarding agents are added to a PVP/nifedipine slush, and the slush is coated onto inert carrier particles. The coated carrier particles are then dried and sieved. The coated particles themselves are then admixed with conventional additives and either compressed into tablets and coated, or placed inside conventional capsules. Erdos et al assert that, because the grinding and milling of the active ingredient is eliminated in this process, the particle size distribution and particle structure of the starting bulk material has no effect on the release profile of the product tablet. However, it should be noted that the particle size distribution and structure of the carrier particles onto which the active ingredient is coated will add statistical fluctuations to the release profile of the finished product.

Similar pharmaceutical compositions and methods are described in the following foreign patent documents: West German Patents No. DE 28 22 882, issued December 1978, and No. DE 31 42 853, issued May 1983; EPO Patents No. 0 047 899, issued March 1982, and No. 0 078 430, issued May 1983; Japanese Patent No 58-109-412, issued June 1983; and Great Britain Patent No. 2 139 892 A, issued November 1984. These foreign patent references are believed to be cumulative to the above-discussed U.S. patent references.

SUMMARY OF THE INVENTION

The present invention provides a novel process to manufacture sustained release tablets of a therapeutically active ingredient. The process involves the preparation of micronized granules containing both active and inactive ingredients, which results in tablets having a smooth and sustained release profile.

The steps involved in the present process include granulation of a therapeutically active agent, such as nifedipine, with inactive ingredients, such as hydroxypropyl cellulose ether. The resultant granules are then dried if necessary, and micronized.

The remaining ingredients to be included in the final product are granulated either separate from, or in the presence of, the micronized particles from the first step. These granules are also dried, if necessary.

The micronized granules from the first step, and the granules from the second step (or the combined granules from the first two steps) are then lubricated with a suitable lubricant, combined with any remaining ingredients such as desiccants, excipients, etc., and compressed into tablets. The resultant tablets have a consistent release profile, good content uniformity, and good bioavailability.

Micronization of the granules formed in the first step ensures a more even distribution of the active ingredient in the finished product because micronization overcomes the effects of differing particle sizes of the active ingredient. Often, a given active ingredient will vary widely in particle size and distribution from supplier to supplier, or from lot to lot of a single supplier. By micronizing the first granules, this effect is minimized, which results in tablets having excellent content uniformity, consistent release profile, and good bioavailability.

The process is especially effective to produce tablets which successfully deliver a therapeutically effective dose of nifedipine. Nifedipine, (dimethyl 1,4-dihydro-2,6-dimethyl-4 -(o-nitrophenyl)-pyridine-3,5-dicarboxylate) is a pharmacologically active agent which affects the circulatory system of humans. It is a member of a class of active compounds generally referred to as dihydropyridines. Being extremely sensitive to light, and highly water-insoluble, nifedipine is a particularly difficult pharmaceutical agent to successfully formulate into a sustained release dosage form having good bioavailability, good content uniformity, and a consistent release profile.

Therefore, it is an objective of the present invention to provide a method to formulate sustained release tablets of a given active agent, having a consistent release profile of the active agent, good content uniformity, and good bioavailability.

It is also an objective of the present invention to provide a method for formulating nifedipine into a sustained release tablet dosage form having a consistent release profile, good content uniformity, and good bioavailability.

Yet another objective of the present invention is to accomplish the above-stated objectives through a simple, straightforward process using conventional equipment.

DETAILED DESCRIPTION OF THE PREFERRED EMBODIMENT

In a preferred embodiment, in a first step nifedipine is granulated in the presence of hydroxypropyl cellulose to yield a first portion of granules. Any known method of granulation can be used to form the granules. The granules may be optionally dried. Drying can be done in any conventional manner, for example, in a fluidized bed dryer.

In a second step, the first portion of granules is then micronized to yield particles ranging in size from 0.1 micrometers to 50 micrometers. Particles falling within this size range are generally referred to as micro-granules. Micronization is performed in any number of commercially available pulverizing devices, such as a jet energy grinding mill. Such devices can be purchased, for instance, from The Jet Pulverizer Company, Palmyra, N.J. 08065, U.S.A.

In a separate process, a second portion of additional inactive substances are granulated to form a second portion of granules. Granulation may be effected by any known method. These granules may be optionally dried.

The second portion of granules is then combined with the micronized particles formed in the second step to yield a mixture. Additives such as desiccants, diluents, glidants, binders, colorants, preservatives, lubricants, etc., may also be optionally added to the mixture. A granulating fluid, such as a hydroalcoholic solution containing alcohols from 5 to 50% in water, is added to the mixture in a quantity sufficient to promote granulation. The resultant final mixture is then compressed into tablets using conventional tablet-forming equipment.

In another embodiment, the micronized particles formed in the second step are granulated along with the second portion of inactive substances. The resultant granules are then combined with any of the desired additives described above, and compressed into tablets.

The active ingredients which can be used in the present process include organic and inorganic medicaments without limitation. The active ingredients include, but are not limited to, water-soluble, semi-soluble, and water-insoluble pharmacologically active agents.

The inactive ingredients of the first portion of granules will be present in an amount within the range of from 4 to 99 percent by weight. Suitable inactive ingredients which can be used in the present process are preferably cellulose polymers. Such cellulose polymers include cellulose ethers such as methyl cellulose, cellulose alkyl hydroxylates such as hydroxyethyl cellulose, hydroxypropyl cellulose, and hydroxypropylmethyl cellulose, and the like; and cellulose alkyl carboxylates such as carboxymethyl cellulose and carboxyethyl cellulose. Povidone (polyvinylpyrrolidone), starches, alginates, acrylate polymers, and the like may also be used. Hydroxypropyl cellulose is preferred.

Lubricants which may be employed in the present invention include commonly used water-soluble and water-insoluble lubricants. Magnesium stearate or stearic acid is preferred. One or more lubricants can be used. The lubricant(s) is present in an amount sufficient to afford smooth tablet formation.

Additionally, the process may optionally employ one or more binders to ensure that the finished tablets have sufficient and long-lasting mechanical integrity. These agents ensure that the finished tablet is structurally sound so that it will remain whole both during shipment and when moving in a fluid stream such as that found in the gastrointestinal tract. Suitable binders include starches such as corn starch and modified corn starch, povidone, acacia, and the like.

Also, the present process may employ additional edible non-active ingredients which are conventionally used in solid pharmaceutical formulations. Such conventional ingredients include preservatives, colorants, stabilizers, anti-adherents, glidants, desiccants, flow control agents, and the like.

EXAMPLES

The following formulations have been used for making the first portion of granules for the sustained release tablets according to the presently claimed process. These examples are included for illustrative purposes only and should not be construed as limiting the claimed invention in any manner.

| | |
|---|---|
| 1. Nifedipine (coarse*) | 96% |
| Povidone | 4% |
| Hydroalcoholic solution - | quantity sufficient to granulate |
| 2. Nifedipine (coarse*) | 80% |
| Hydroxypropyl cellulose | 20% |
| Hydroalcoholic solution or water - | quantity sufficient to granulate |
| 3. Nifedipine (coarse*) | 80% |

-continued

| | |
|---|---|
| Hydroxypropyl-methyl cellulose | 20% |
| Hydroalcoholic solution or water - | quantity sufficient to granulate |
| 4. Nifedipine (coarse*) | 70% |
| Hydroxypropyl-methyl cellulose | 20% |
| Hydroxypropyl cellulose | 10% |
| Hydroalcoholic solution - | quantity sufficient to granulate |

*Specific surface area is less than 1 m²/gram

It is to be understood that the present invention is not limited to the embodiments described above, but encompasses any and all embodiments within the scope of the following claims.

We claim:

1. A process to manufacture sustained release tablets containing nifedipine comprising the steps of:
   wet granulating at nifedipine in the presence of at least one inactive substance to form a first portion of granules;
   micronization of said first portion of granules to form micro-granules;
   separately granulating at least one inactive substance to form a second portion of inactive granules separate from said first portion of granules;
   combining said micro-granules and said second portion of inactive granules to form a mixture; and
   compressing said mixture to form tablets.

2. The process according to claim 1, wherein said at least one inactive substance forming said first portion of granules and said second portion of inactive granules is selected from the group consisting of starches, alginates, acrylate polymers, cellulose ethers, cellulose alkyl hydroxylates, and cellulose alkyl carboxylates.

3. The process according to claim 1, wherein said at least one inactive substance forming said first portion of granules and said second portion of inactive granules is selected from the group consisting of methyl cellulose, hydroxyethyl cellulose, hydroxypropyl cellulose, hydroxypropylmethyl cellulose, carboxymethyl cellulose, and carboxyethyl cellulose.

4. The process according to claim 3, wherein said at least one inactive substance is a combination of hydroxypropyl cellulose and hydroxypropylmethyl cellulose.

5. The process according to claim 1, wherein said at least one inactive substance is hydroxypropyl cellulose.

6. The process according to claim 1, wherein said at least one inactive substance is hydroxypropylmethyl cellulose.

7. The process according to claim 1, wherein said at least one inactive substance is povidone.

8. The process according to claim 1, further comprising treating said mixture with a lubricant prior to compressing said mixture.

9. A process to manufacture sustained release tablets containing nifedipine comprising the steps of:
   wet granulating nifedipine in the presence of at least one inactive substance to form a first portion of granules;
   micronization of said first portion of granules to form micro-granules;
   then granulating at least one inactive substance in the presence of said micro-granules to form a mixture; and
   compressing said mixture to form tablets.

10. The process according to claim 9, wherein said at least one inactive substance forming said first portion of granules and said second portion of inactive granules is selected from the group consisting of starches, alginates, acrylate polymers, cellulose ethers, cellulose alkyl hydroxylates, and cellulose alkyl carboxylates.

11. The process according to claim 9, wherein said at least one inactive substance forming said first portion of granules and said second portion of inactive granules is selected from the group consisting of methyl cellulose, hydroxyethyl cellulose, hydroxypropyl cellulose, hydroxypropylmethyl cellulose, carboxymethyl cellulose, and carboxyethyl cellulose.

12. The process according to claim 11, wherein said at least one inactive substance is a combination of hydroxypropyl cellulose and hydroxypropylmethyl cellulose.

13. The process according to claim 9, wherein said at least one inactive substance is hydroxypropyl cellulose.

14. The process according to claim 9, wherein said at least one inactive substance is hydroxypropylmethyl cellulose.

15. The process according to claim 9, wherein said at least one inactive substance is povidone.

16. The process according to claim 9, further comprising treating said mixture with a lubricant prior to compressing said mixture.

17. A process for manufacturing micronized nifedipine granules having improved content uniformity, wetability, and bioavailability comprising the steps of:
   blending coarse nifedipine crystals with at least one inactive hydrophilic substance to form a blend;
   wet granulating the blend to form granules;
   drying the granules to form dried granules; and
   micronizing the dried granules to form micronized nifedipine granules.

18. The process according to claim 17 wherein said at least one inactive substance is selected from the group consisting of povidone, starches, alginates, acrylate polymers, cellulose ethers, cellulose alkyl hydroxylates, and cellulose alkyl carboxylates.

19. The process according to claim 17 wherein said wet granulating is carried out in an aqueous solution.

20. The process according to claim 19 wherein said aqueous solution is a hydroalcoholic aqueous solution.

21. The process according to claim 17 wherein said drying is performed in one of the group selected from an oven, a fluid bed drier, and a microwave dryer; and said micronizing is performed in an airjet mill.

* * * * *